United States Patent [19]

Gala

[11] Patent Number: 4,762,134

[45] Date of Patent: Aug. 9, 1988

[54] VERTEBRAE DIAGNOSTIC AND TREATMENT APPARATUS

[76] Inventor: Jeffery Gala, 3000 N. Ocean Dr., Suite 28G, Singer Island, Fla. 33404-3249

[21] Appl. No.: 891,561

[22] Filed: Aug. 1, 1986

[51] Int. Cl.⁴ ............................................. A61B 5/10
[52] U.S. Cl. ................................................... 128/781
[58] Field of Search ................ 128/774, 781, 782, 51, 128/52, 53

[56] References Cited

U.S. PATENT DOCUMENTS

| | | | |
|---|---|---|---|
| 3,209,748 | 10/1965 | Thomas | 128/53 |
| 3,277,887 | 10/1966 | Thomas | 128/53 |
| 4,041,938 | 8/1977 | Wintoniw | 128/52 |

Primary Examiner—Edward M. Coven
Assistant Examiner—J. P. Lacyk
Attorney, Agent, or Firm—Basile Hanlon

[57] ABSTRACT

A vertebrae diagnostic and treatment apparatus. The diagnostic and treatment apparatus includes a controller having inputs selecting various modes of operation of the controller and an indicator providing a display of the initial movement of the vertebrae and the subsequent movement under applied force from the diagnostic and treatment apparatus. A patient engaging device driven by the controller includes a plurality of extensible pads mounted externally on a portable housing. A force detection device, such as a load cell with accelerometer, is mounted within the housing in conjunction with each pad to detect the amount of resistance applied to each pad by the vertebrae of the user. A drive source, such as an electrically operated solenoid, causes extension and retraction of each pad in any desired mode, such as simultaneous, oscillatory or alternating in order to apply a pre-determined amount of force and direction of force to the vertebrae of a patient through the pads to provide diagnosis and treatment for vertebrae mechanical dysfunction.

6 Claims, 3 Drawing Sheets

VERTEBRAE DIAGNOSTIC AND TREATMENT APPARATUS

BACKGROUND OF THE INVENTION

1. Field of the Invention

This invention relates, in general, to medical diagnostic and treatment devices and, more specifically, to chiropractic/medical diagnostic and treatment devices for use in discovering and correcting dysfunction of vertebrae mechanics.

2. Description of the Prior Art

Various problems occur with vertebrae or joints in the spines of human beings. A primary cause of such vertebrae or joint dysfunction involves the fibrous ligaments which maintain the joints of the vertebrae in a bone-to-bone relationship.

Long term of accommodation to a disarticulation of the joint caused by a variety of external forces and other problems results in a stretching of certain fibers of the ligaments surrounding the joint accompanied by a contraction or compression of the opposed ligaments of the same joint transversely about the rotational axis of the joint. This causes not only discomfort but could also lead to potentially dangerous adaptation to such joint degeneration, with consequential patient problems relating to the spine. In order to overcome these problems, the contracted ligamentous fibers must be re-stretched to provide a more proper alignment of the joints articular facets of the vertebrae.

Manual manipulation by a trained physician has long been employed by applying an indirect force to two contiguous segments of a joint in the vertebrae to re-stretch the contracted ligaments. Such manual techniques are fraught with hazard due to the lack of both control and repeatability and commonly provide inadequate results or excessive damage to the tissue surrounding many joints of the vertebrae. The inherent danger of manual manipulation of the vertebrae is based on the possible lack of both the skill and experience of the physician.

Also, there is no currently available piece of analytic equipment which can provide information to the physician of the amount of dysfunction of the joint and/or the effectiveness of the application of any treatment to the dysfunctioning joint. This would be extremely useful to the physician insofar as enabling him or her to adopt the best treatment for a particular patient without causing further damage to the force absorbing tissues surrounding the vertebrae joints of the patient.

Thus, it would be desireable to provide a diagnostic and treatment device for particular use with a dysfunctioning vertebrae which overcomes the problems of previously employed methods used to treat dysfunctioning vertebrae. It would also be desirable to provide a vertebrae diagnostic and treatment device which is easily used and which indicates the amount of dysfunctioning of a particular joint in the vertebrae. It would also be desirable to provide a vertebrae treatment device in which a dysfunctioning joint of the vertebrae of a patient can be treated by applying a particular amount of force at a desired location on the vertebrae.

SUMMARY OF THE INVENTION

The present invention is a vertebrae diagnostic and treatment apparatus which is useful in diagnosing the extent of dysfunction in the vertebrae of a human being and applying a force to a selected joint of the vertebrae to treat such a dysfunction. The diagnostic and treatment apparatus includes a controller having several inputs which control the operation of the diagnostic and treatment apparatus and a display, such as an oscilloscope, which provides a visual indication of the amount of dysfunction of the joint and the amount of force and resulting movement of this joint during treatment. A patient engaging means driven by the controller includes a plurality of paddles which are extensibly mounted externally on a portable housing. Force detection devices, such as load cells coupled with accelerometers, are mounted within the housing in registry of each pad to detect the amount of force applied to each pad and indirectly the amount of movement of the joint of the patient and vertebrae which the pad contacts.

A drive means, such as an electrically operated solenoid, is attached to each pad and causes extensible and retractable movement of each pad with respect to the housing. Preferably, the solenoids are operated by the controller in an oscillatory, alternating manner to apply a pre-determined amount of force on either side of the joint of the vertebrae of the patient to cause movement of a particular joint of the vertebrae of the patient. In the diagnostic mode, the housing is placed on the patient's back and solenoid activated movement of the pads results in forces being applied to the vertebrae of the patient. The output from the load cells are input to the controller which displays the patient presented initial amount of motion or, twisting movement of the particular joint of the vertebrae being evaluated. This is used as a base or reference signal from which progress can be measured during subsequent treatment.

In the treatment mode, the drive means in the housing is activated to cause a selected joint oscillation by opposing the alternating extension and retraction of the pads from each of the two housings. This applies forces to the isolated joint of the patient's vertebrae resulting in the pre-determined amount of movement of the joint. This aids in stretching the contracted ligaments uniquely "within their elastic limits" as well as breaking free any adhesions, etc., all well known to physicians working with mechanical dysfunctioning vertebrae. The resultant forces and the amount of twisting movement of the vertebrae as caused by the extension of pads in the housing are also displayed on the indicator or real time feedback monitor/recorder to aid the physician in continuance of both ongoing and further treatment of the same patient condition.

The vertebrae diagnostic and treatment apparatus of the present invention overcomes many of the problems encountered with previous treatment methods for vertebrae dysfunctioning; since it forms a previously unavailable detection apparatus. Initially, the vertebrae detection and treatment apparatus of this invention is deployed in a single compact unit which makes it easily portable and is safely applicable to a patient. It can also be mounted in an overhead stand with lockable positioning arms which will hold the two housings or end effectors over the patient lying prone on a table underneath the apparatus.

The operation of the detection and treatment device including the force, application of the forces, etc., is variable which aids in its application to patients with varying levels of vertebrae dysfunction.

BRIEF DESCRIPTION OF THE DRAWING

The various features, advantages and other uses of the present invention will become more apparent from the following description and drawing in which.

DESCRIPTION OF THE PREFERRED EMBODIMENTS

Figure 3:
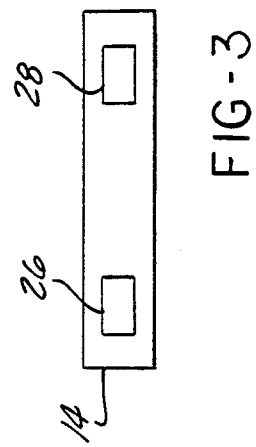
FIG. 3 is a bottom view of the user engaging means shown in FIG. 2 but in full elevation.

Throughout the following description and drawing, an identical reference number is used to refer to the same component in multiple figures of the drawing.

Figure 1:
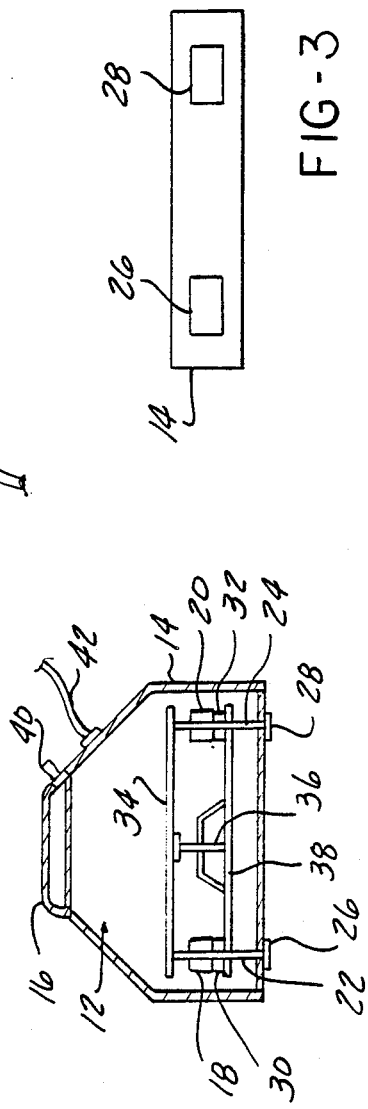
FIG. 1 is a front elevational view of the controller/monitor employed in the diagnostic and treatment apparatus of the present invention.

As shown in the drawing and, in particular, in FIG. 1 there is illustrated a vertebrae diagnostic and treatment apparatus 10 which is useful in diagnosing the extent of movement of a patient's vertebral joints to detect the magnitude and extent of any existing mechanical lesions, to the patient's vertebrae as well as providing treatment for any such vertebrae related problems via restoration of lost motion.

Figure 2:
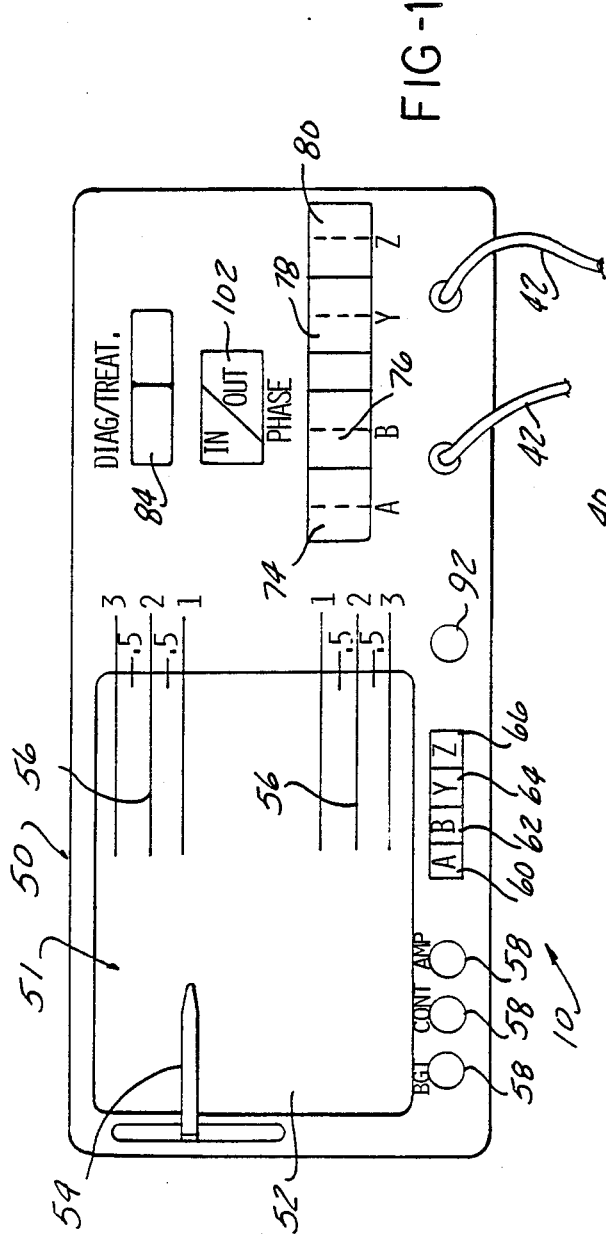
FIG. 2 is a central, cross sectional view of the patient engaging means employed in the diagnostic and treatment apparatus of the present invention.

The diagnostic and treatment apparatus 10 includes a patient engaging means 12 which is placed on the back of a patient so as to engage the vertebrae of the patient. The patient engaging means 12, as shown in FIG. 2, includes a housing 14. A handle 16 is mounted on the top end of the housing 14 for mounting or hanging the housing 14 on a convenient support surface when not in use.

Mounted within the interior of the housing 14 are a plurality of drive means, such as electro-mechanical solenoids 18 and 20, two of which are shown in FIGS. 2 and 3. Each solenoid 18 and 20 includes an energizable electromagnetic coil, not shown, and an extensible and retractable shaft or rod 22 and 24, respectively. The rods 22 and 24 extend outwardly through the housing 14.

Each user engagement member, such as a resilient pad 26 and 28, is mounted on the outer end of each shaft or rod 22 and 24, respectively, exteriorly from the housing 14. The pads 26 and 28 are spaced apart on the bottom surface of the housing 14 and may have any desired shape, such as square, rectangular, circular, etc.; although a rectangular shape is preferred for maximum surface area engagement of the user's vertebrae. Further, the pads 26 and 28 are formed of a resilient material to facilitate comfortable contact with the patient's vertebrae.

As shown generally in FIG. 2, a load or force sensing means 30 and 32, such as a conventional load cell with or without an accelerometer, is mounted in registry with each solenoid 18 and 20, respectively, and has its output connected to a controller 50, described hereafter, to provide an indication that the amount of force imparted on the pads 26 and 28 when the diagnostic and treatment device 10 is positioned on a particular joint of the vertebrae of a patient.

A support structure in the form of a plate 34 is mounted within the housing 14. A pivotally mounted shaft 36 extends from the plate 34 and is attached to a second plate 38. The second plate 38 supports the shafts 22 and 24 of the solenoids 18 and 20, respectively, for the option of a locked static or free pivotal movement with respect to the housing 14.

A switch 40 is mounted on the housing and is electrically connected to the controller 50 to enable activation of the patient engaging means 12. A conductor 42 extends from the housing and is connectable via a plug-in connection to the controller 50 to provide the necessary electrical connections for the controller 50 to activate and monitor the user engaging means 12.

Figure 4:
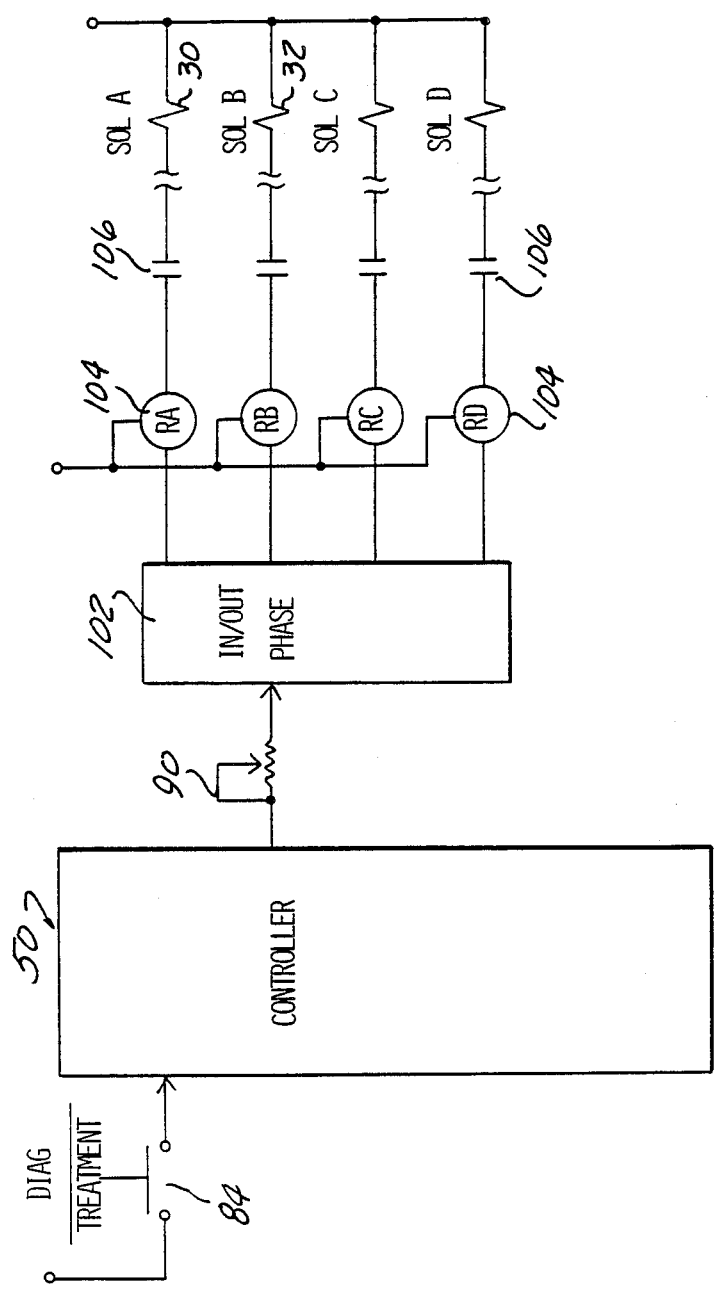
FIG. 4 is a schematic representation of the circuitry employed to activate the solenoids attached to the pads in the user engaging means.
Figure 5:
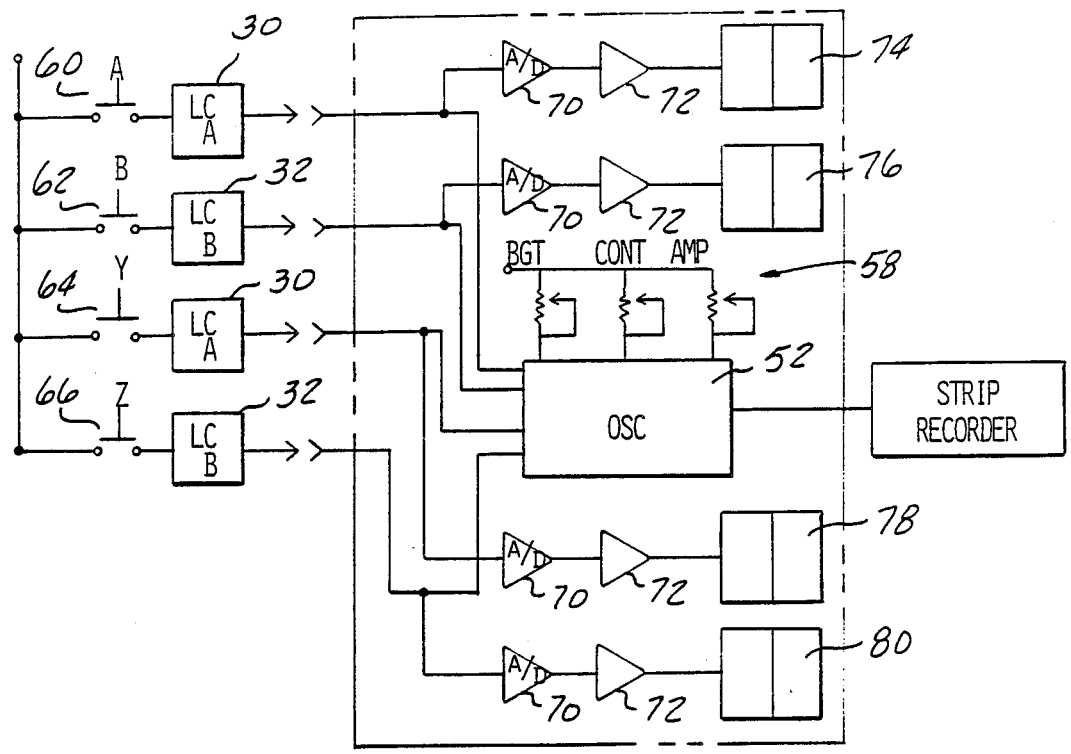
FIG. 5 is a schematic diagram showing various indicators employed in the controller of the present invention.

Referring now to FIGS. 1, 4 and 5, there is illustrated a pictorial representation and detailed schematic of the controller 50 which operates the user engaging means 12. The controller 50 includes a control panel 51 having an oscilloscope monitor 52 mounted therein. Preferably the oscilloscope 52 has memory recall for displaying the magnitude of certain signals which have occurred during previous use of the diagnostic and treatment device 10. A slidable marker 54 is mounted on the face of the control panel 51 adjacent one side of the oscilloscope screen 52. The marker 54 provides an indication of the initial amplitude reading received from the selected load cells 30 and 32. The opposed side of the screen of the oscilloscope 52 is provided with gradations 56 to provide an end amplitude reading from the selected load cells 30 and 32 after force has been applied to the vertebrae of the patient through the housing 12. Conventional lightness, contrast and amplitude controls 58 are provided on the control panel 51 to provide ease of operation of the oscilloscope 52.

The control panel 51 is provided with a switch labeled diagnostic/treatment 84 which selects between the two modes of operation of the controller 50. As shown in FIGS. 1 and 4, the diagnostic/treatment switch 84 is input to the controller 50.

Figure 6:
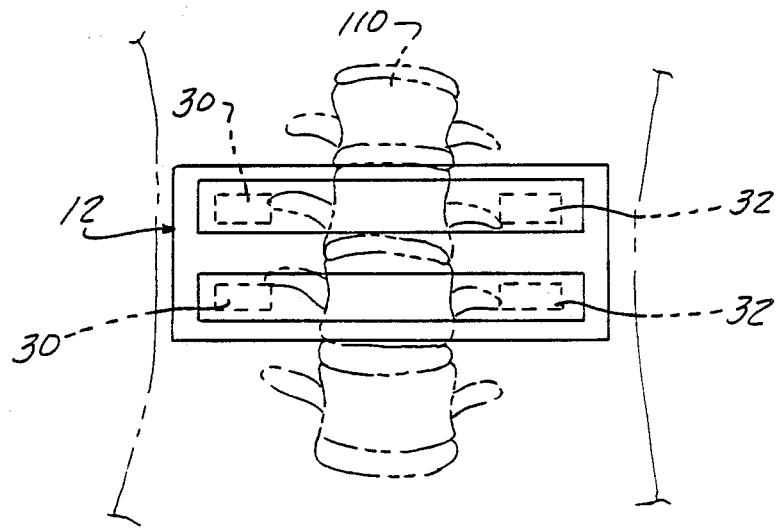
FIG. 6 is a plan view of the application of the housing and the pad means over the vertebrae of a patient as employed according to the teachings of the present invention.

Although only two pads 26 and 28 are illustrated in FIG. 2 as being mounted on the housing 12, it will be understood that, preferably, four pads or two separate housings be arranged in a square configuration by a secondary housing 12 for optimum results as shown in FIG. 6. The four pads are individually selected by the switches 60, 62, 64 and 66 mounted on the control panel of the controller 50 for selective operation depending upon the desired therapy for the patient. As shown in FIG. 5, the switches 60, 62, 64 and 66 are electrically connected to the load cells 30 and 32 attached to the pads. The output from the load cells 30, 32 are connected to the controller 50 through individual A/D converters 70 and amplifiers 72 for each load cell 30, 32 to a display 74 or 76, respectively for each pad or load cell 30, 32. This provides a display of the amount of force exerted which is useful to the physician in providing diagnostic and treatment of a particular vertebrae dysfunction.

As shown in FIG. 4, a frequency adjustment 90 in the form of a potentiometer is connected to an output of the controller 50 and input to an in/out phase circuit 102. The in/out phase circuit 102 provides movement of the pads of each housing to move simultaneously in and out of the housing in a left/right manner, or in a oscillating-/alternating manner of left/right, right/left as selected by the physician. The outputs from the in/out phase circuit 102 are connected to individual relays 104 having movable contacts 106 connected to electro-mechanical solenoids forming a part of the user engageable means 30 and 32. The solenoids 30 and 32 drive the pads 26 and 28 in a rate set by the frequency adjustment means 90 and the in/out phase circuit 102. This can be such that all of the pads 26 and 28 are extended simultaneously into engagement with the user's vertebrae alternatingly, or in any other desired pattern depending upon the therapeutic program devised by the physician. The in/out phase circuit 102 controls by way of the frequency adjustment 90 the activation of the relay 104 to selectively open and close its associated contacts 106 and thereby energize the solenoids 18 and 20 attached to the pads 26 and 28. This provides selective detection and movement of the joints in the vertebrae 110 of a patient as shown in FIG. 6.

In use, the housing 12 is placed on the back of a patient with the pads 26 and 28 positioned on the opposing sides of a desired vertebrae joint. In the diagnostic mode, the pads 26 and 28 through the load cells 18 and 20 upon activation of the solenoids 30 and 32 are extended and generate an output signal corresponding to the amount of twisting or movement of the selected joint of the vertebrae 110. This is input to the controller 50 as shown in FIG. 5 through selection of the various load cell/accelerometer selection switches 60, 62, 64 and 66. An indication of the amount of relative movement is provided by the indicators 74, 76, 78 and 80 as selected by the switches 60, 62, 64 and 66. The oscilloscope provides an indication which may be used with the marker 54 to provide an initial indication of the relative movement of a particular joint in the vertebrae 110 of the patient. In the treatment mode, when it is desired to apply a force and thereby provide therapeutic movement of a particular joint of the vertebrae 110, the pads 26 and 28 are now extended to apply a corrective force to restore the recognized loss of motion in the joint of the vertebrae 110. This may be selected by the in/out phase circuit 102 and the frequency circuit 90 in any desired rate and pattern. The pattern of activation of the pads 26 and 28 may be simultaneous, alternating or oscillatory as desired by the physician's care plan to overcome the amount of dysfunction found in the vertebrae 110 of the patient. For example, the pads 30 and 32 shown in FIG. 6 may be activated in an alternating pattern at a particular rate as described above.

This provides a force to the vertebrae 110 of the patient which causes stretching of the fibrous ligaments comprised in each joint of the vertebrae to overcome previous vertebrae dysfunction problems. The amount of time, frequency, amplitude and the pattern of application of the pads 30 and 32, FIG. 6, can be easily selected by the physician through the controller 50 depending upon the particular patient's condition.

The housing 12 of this invention may also be rigidly mounted from an overhead support overhanging a conventional vibratory or shaker table on which the patient lies. The pads 26 and 28, FIG. 1, are operated in the manner described above in the diagnostic mode. However, in the treatment mode the pads 26 and 28 are fixedly extended in any patterns into contact with a selected vertebrae with vibratory movement and the force applied to the vertebrae being supplied by the shaker table.

What is claimed is:

1. A diagnostic and treatment apparatus for use on the vertebrae of a patient having a plurality of interconnected joints comprising:
   means for engaging the vertebrae of a patient including;
   a housing;
   a plurality of pads spacedly, extensibly and retractably mounted in the housing; and
   drive means connected to said pads for individually extending and retracting each of the plurality of the pads into and out of engagement with the vertebrae of a patient;
   means connected between said drive means and said pads for sensing the resistance of said vertebrae by measuring a force applied by the pads to the vertebrae of the patient; and
   a control means connected to said housing, responsive to the sensing means, for controlling the operation of the drive means to measure an initial force that is applied to the vertebrae and for controlling the drive means to apply an amount of force to the vertebrae that is dependent upon the resistance of the vertebrae as measured by said sensing means.

2. The diagnostic and treatment apparatus of claim 1 wherein the drive means comprises an electro-mechanical relay connected to an electric solenoid attached to the pad.

3. The diagnostic and treatment apparatus of claim 1 wherein the plurality of pads are two pads mounted in the housing at spaced locations.

4. The diagnostic and treatment apparatus of claim 3 wherein the pads are driven in an opposite, reciprocating manner by the drive means.

5. The diagnostic and treatment apparatus of claim 1 wherein the control means comprises:
   input means, associated with the means for engaging the vertebrae of a patient, for activating the drive means; and
   indicator means for indicating the amount of force applied by the pads to the vertebrae of the user.

6. The diagnostic and treatment apparatus of claim 1 wherein the pads include force detecting means.

* * * * *